(12) United States Patent
Stein et al.

(10) Patent No.: US 10,273,607 B2
(45) Date of Patent: Apr. 30, 2019

(54) DECORATIVE GRADUATED COMPRESSION SOCK

(71) Applicants: Celeste Stein, Galveston, TX (US); Rodney Dana Mabe, Ellerbe, NC (US)

(72) Inventors: Celeste Stein, Galveston, TX (US); Rodney Dana Mabe, Ellerbe, NC (US)

(*) Notice: Subject to any disclaimer, the term of this patent is extended or adjusted under 35 U.S.C. 154(b) by 0 days.

(21) Appl. No.: 15/648,479

(22) Filed: Jul. 13, 2017

(65) Prior Publication Data
US 2019/0015259 A1    Jan. 17, 2019

(51) Int. Cl.
    *D04B 1/26*      (2006.01)
    *A61F 13/08*     (2006.01)
    *D04B 35/36*    (2006.01)

(52) U.S. Cl.
    CPC .............. *D04B 1/265* (2013.01); *A61F 13/08* (2013.01); *D04B 35/36* (2013.01)

(58) Field of Classification Search
    CPC ... D04B 1/26; D04B 1/246; D04B 9/46–9/56; D04B 1/265
    See application file for complete search history.

(56) References Cited

U.S. PATENT DOCUMENTS

| | | | | |
|---|---|---|---|---|
| 4,015,448 A * | 4/1977 | Knohl | ....................... | D04B 9/52 66/178 A |
| 4,027,667 A * | 6/1977 | Swallow | .................. | D04B 9/52 602/63 |
| 4,172,456 A * | 10/1979 | Zens | ........................ | A61F 13/08 2/240 |
| 4,180,065 A * | 12/1979 | Bowen | ..................... | A61F 13/08 2/239 |
| 4,502,301 A * | 3/1985 | Swallow | ................. | A61F 13/08 602/62 |
| 6,012,177 A * | 1/2000 | Cortinovis | .............. | A61F 13/08 2/239 |
| 6,092,397 A * | 7/2000 | Cortinovis | ............. | A41B 11/00 2/239 |
| 6,123,681 A * | 9/2000 | Brown, III | ............. | A61H 23/02 2/239 |
| 6,430,970 B1 * | 8/2002 | Gardon-Mollard | ..... | A61F 13/08 66/178 A |
| 6,725,691 B2 * | 4/2004 | Yakopson | ............... | A61F 13/08 2/240 |
| 7,895,863 B2 * | 3/2011 | Smith | ..................... | A61F 13/08 66/172 E |
| 7,950,071 B2 | 5/2011 | Jeong | | |
| 8,234,885 B2 * | 8/2012 | Smith | ..................... | A61F 13/08 66/172 E |
| 8,731,703 B1 * | 5/2014 | Lehrer | .................. | G06F 3/1257 700/132 |

(Continued)

*Primary Examiner* — Danny Worrell
(74) *Attorney, Agent, or Firm* — Delphine James (57) ABSTRACT

The present invention provides a decorative compression sock made from resilient elastic material for the prevention and treatment. The material is composed of a plurality of fibers. An aesthetically pleasing image is stored onto a sublimation transferable medium. The image is transferred from the sublimation transfer medium onto the compression sock wherein the image is permanently incorporated into the plurality of fibers of the material. The compression sock configured as a knee length tubular member having a closed end and an opened lower end. Compression is graduated from the toe, ankle and leg portion.

18 Claims, 8 Drawing Sheets

(56) References Cited

U.S. PATENT DOCUMENTS

| | | |
|---|---|---|
| 9,777,413 B2* | 10/2017 | Messier .................. D04B 9/52 |
| 2005/0252392 A1 | 11/2005 | Kim et al. |
| 2007/0113593 A1 | 5/2007 | Jeong |
| 2012/0102613 A1 | 5/2012 | Loth et al. |
| 2016/0251782 A1* | 9/2016 | Liao ........................ D04B 1/18 |
| | | 66/202 |

* cited by examiner

DECORATIVE GRADUATED COMPRESSION SOCK

This patent claims benefit of provisional application 62/254,092 and 62/306,117

BACKGROUND

The present invention is directed to a compression sock for the prevention and treatment of venous disorders such as edema, phlebitis and thrombosis. Compression stockings are elastic garments worn around the leg, compressing the limb. This reduces the diameter of distended veins and causes an increase in venous blood flow velocity and valve effectiveness. Compression therapy helps decrease venous pressure, prevents venous stasis and impairments of venous walls, and relieves heavy and aching legs.

The design of a sock, especially a sock for the treatment of venous disorders, can have a huge effect on the wear's comfort and well-being. Knee high compression hose are used not only to help increase circulation, but to also help prevent the formation of blood clots in the lower legs, as well as aiding in the treatment of ulcers of the lower legs. Unlike traditional socks, compression socks use stronger elastics to create significant pressure on the legs, ankles and feet. Compression stockings are tightest at the ankles and gradually become less constrictive towards the knees and thighs. By compressing the surface veins, arteries and muscles, the circulating blood is forced through narrower circulatory channels. As a result, the arterial pressure is increased, which causes more blood to return to the heart and less blood to pool in the feet.

The compression sock that are on the market have thicker yarn such as rubber than normal hosiery and are not as aesthetically pleasing. The present invention provides a softer design compression sock with a desired selected design incorporated therein.

SUMMARY

The present invention is directed to a decorative and printed compression sock, primarily for the treatment and prevention of venous disorders.

The compression sock comprises a generally elongated body made from soft, flexible, resilient, and elastic material. The body of the sock is configured to stretch when placed about a foot, ankle joint and leg and exert compressive pressure thereupon.

In a preferred embodiment, the compression sock has a closed toe end and an opened upper end.

In the preferred embodiment the yarn is made of a composite spandex, nylon and microfiber composite blend. In the preferred embodiment a four feed yarn is provided to a hosiery knitting machine with an alternative needle positive float selection. The tubular sock is created. After creation of the tubular sock, a selected aesthetically pleasing image is stored onto a sublimation transferable medium. The image is transferred from the sublimation transfer medium onto the compression sock wherein the image is permanently incorporated into the plurality of fibers of the material. Sublimation is the process generally used to transfer the image to the fibers of the material. The present invention utilizes the sublimation process to create a new decorative compression sock.

Other features and advantages of the present invention will become apparent from the following more detailed description, taken in conjunction with the accompanying drawings which illustrate, by way of example, the principles of the invention.

BRIEF DESCRIPTION OF DRAWINGS

The accompanying drawings illustrate the invention. In such drawings.

DETAILED DESCRIPTION

The present invention is directed to a compression sock for the prevention and treatment of venous disorders. More specifically, the compression sock has features that address disorders such as edema, phlebitis and thrombosis, among other injuries.

Figure 1:
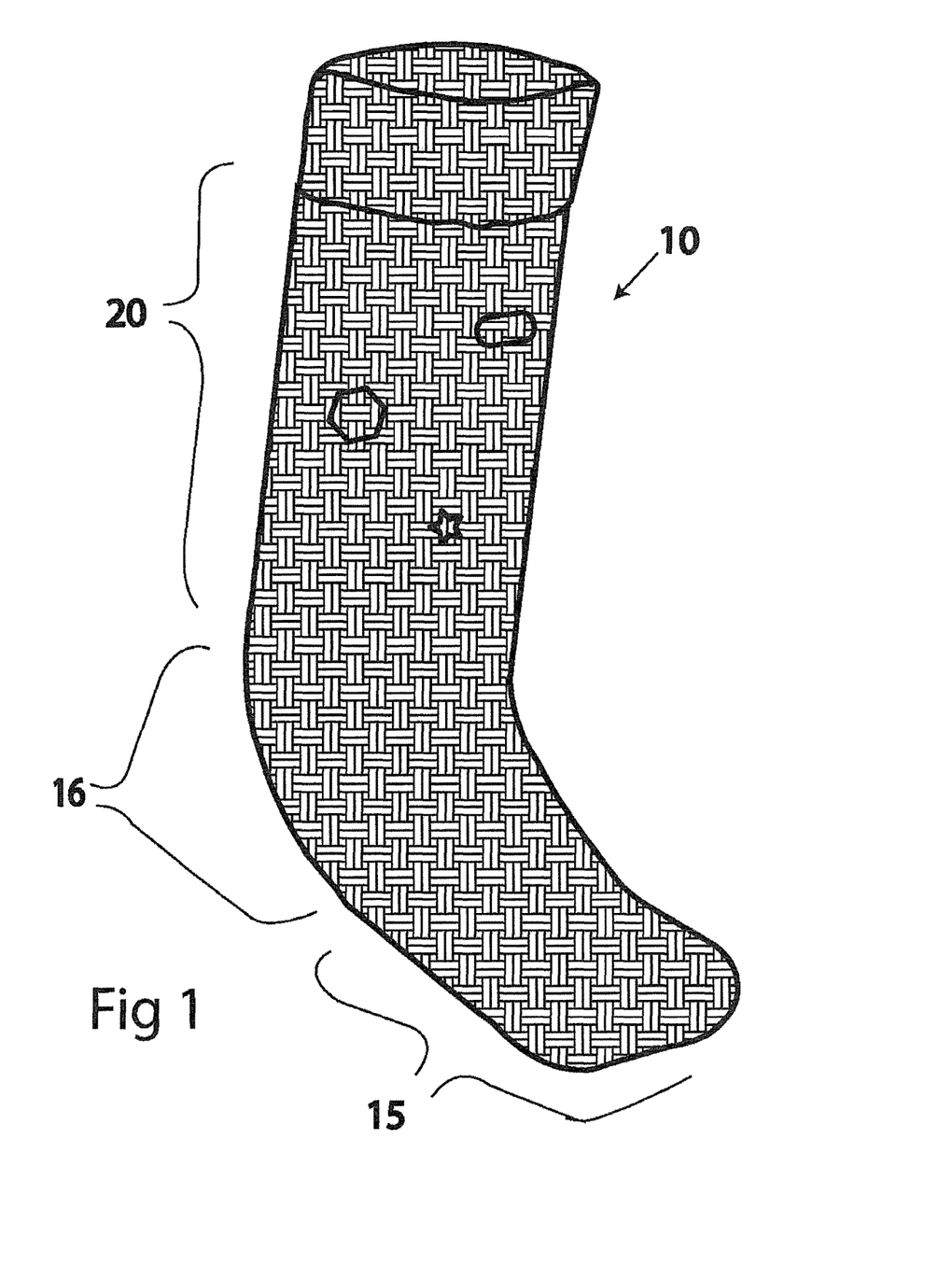
FIG. 1 is a full length tubular sock design embodiment.
Figure 3:
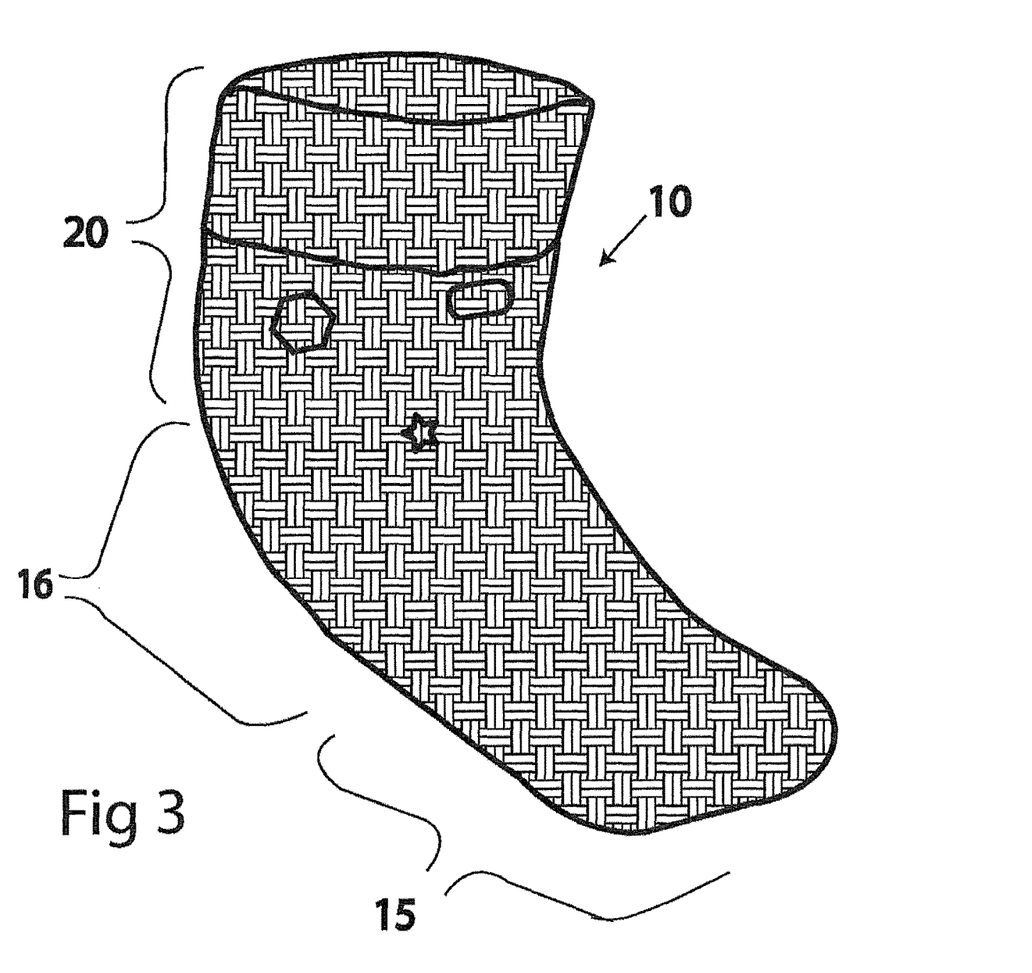
FIG. 3 is an short above ankle tubular sock design embodiment.
Figure 4:
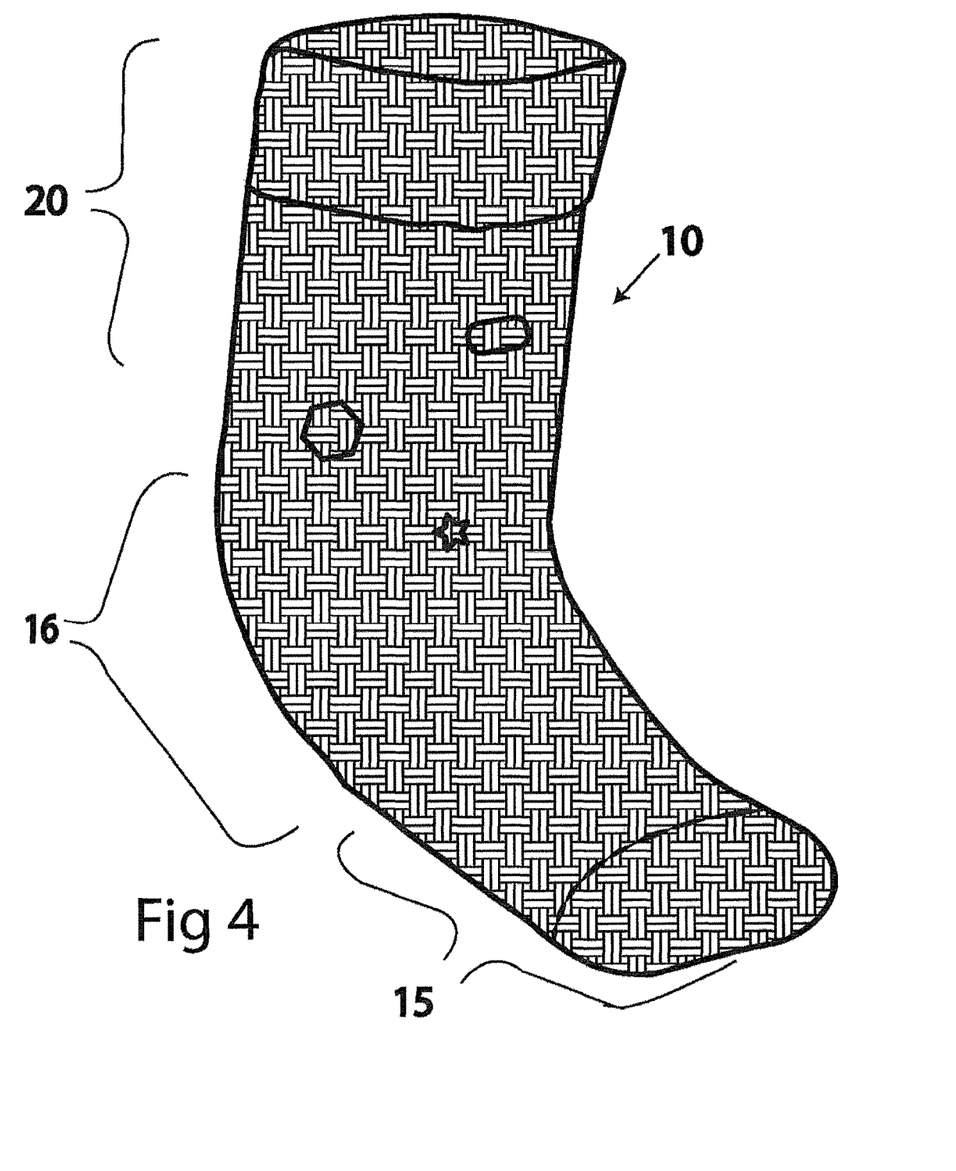
FIG. 4 is an alternative ankle tubular sock design embodiment.

FIG. 1 generally illustrates one embodiment of the design compression sock (10) of the present invention. In the illustrated embodiment the compression sock may be configured generally similar to other socks having an upper calf portion (20), an ankle portion (16), a toe portion (15) with a closed end. In an alternate embodiment of design compression sock (10) illustrated in FIG. 4, the calf portion (20) may be minimized or even further shorten as shown in FIG. 3.

Figure 5:
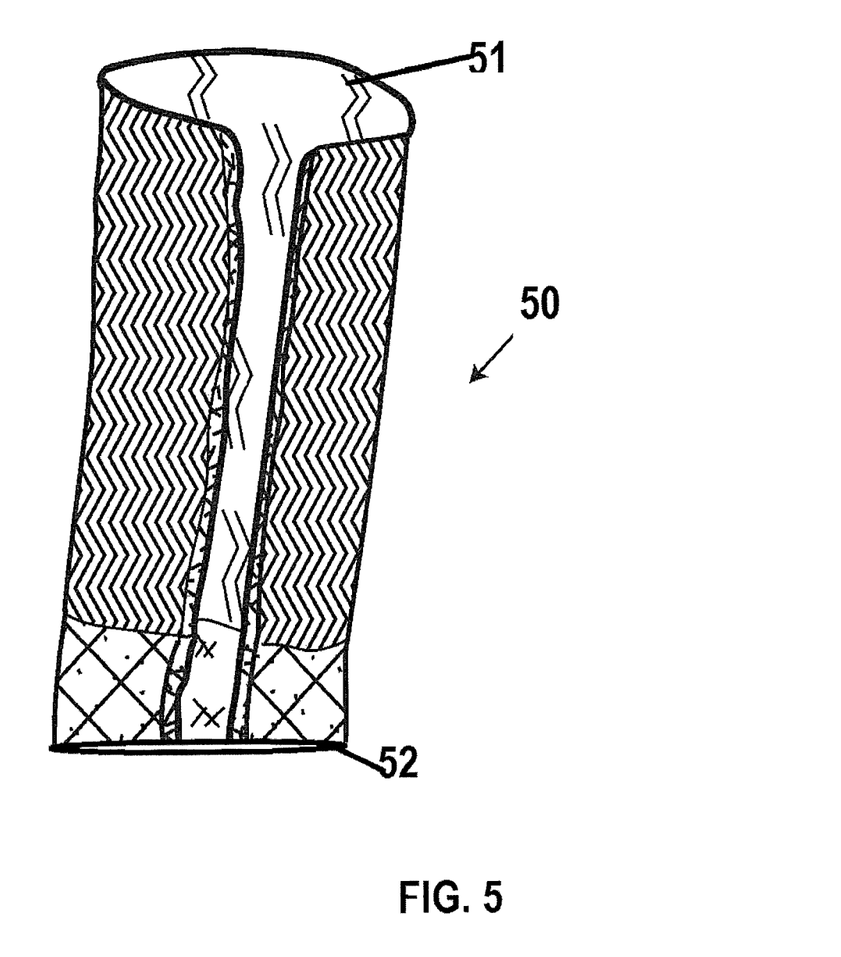
FIG. 5 is an arm tubular sock design embodiment.

Alternatively a design compression sock can be created for the arm which comprises a tubular thin sock (50) with opposing opened ends (51, 52) as shown in FIG. 5. The design is incorporated into this sock with the same process as described below. The sock is preferably constructed to be seamless out of washable and breathable materials. The arm sock is created with graduated compression with the same composite material as the tubular sock as described below. Additionally, the elbow section of the sock (50) can have a different compression than the opposing ends.

Referring to FIG. 1 the present invention is made to initially include a one-piece tubular fabric "sock" structure that includes a closed distal end section, an open proximal end section (20) and an intermediate section (16). The tubular sock (10) is thin and has no heel delineations. Alternatively the tubular sock (10) in FIG. 1 can be redesigned with an opened distal end section for the arm as shown in FIG. 5.

With this embodiment, a ladies hosiery knitting machine is used with a circular needle configuration. The knitting machine is preferably a 70 or 75 gauge knitting machine. In this embodiment the hosiery machine may comprise at least 400 needles on each yarn feed on at least four yarn feed paths. The positive float needle selection provides for stabilizing areas during the knitting process of the unitary seamless tubular body. Tubular structure (10) in FIG. 1 is made of a composite yarn having spandex, micro fiber, nylon or a combination thereof. The spandex yarn can be covered or non-covered. Micro-fiber can be most commonly made of polyester, polyamedes (e.g. nylon, Kevlar, nomex, trogamide), polypropylene or a combination thereof. In the preferred embodiment the micro-fiber is made of nylon and can be made of polyester. The final composite blend is strong, thin, smooth and comfortable to the skin. Various alternative needle positive float stitch selection combination can be utilized to provide stability while providing enhanced stretchability. In the illustrated embodiment in FIG. 6, the knitting machine is programmed to with the at least four feeds thereby creating a fabric structure that is easier to place upon the foot. In the illustrated embodiment, (a) first yarn feed (60) is 70 deniers single covered 30 deniered nylon with 34 filaments (i.e. micro fiber) with a positive float stitch having needles alternating (up:down;up:down) wherein only 200 needles are utilized (b) second yarn feed (70) is 50 (deniered) and 30 (filaments) nylon (i.e. not micro fiber) with all needles up (c) third yarn feed (80) is 70% spandex single covered 30/34 with needles alternating (down:up; down:up); and fourth yarn feed (85) is 50/34 nylon with all needles up. In this illustrated embodiment the first and the third feed are alternating positive floats where the $2^{nd}$ and the $4^{th}$ yarn feeds are flat stitching. The needle selection alternative positive float configuration in conjunction with yarn selection produces a tubular sock that is thin, softer, slicker and easier to place on the foot. Additionally, the yarn and needle selection produces a tubular sock in which the design can be more easily, efficiently, effectively and permanently incorporated into the tubular sock design. As shown in Feed 1 (60) and Feed 3 (80) 200 needles (75) is up with an adjacent needle down next to sinker (76). Additionally depicted is Feed 2 and Feed 4, 400 needles (75) are all up.

As used herein, "seamless" means that the construction of the sock does not include any stitching to join two or more pieces of material together. A hem or border is located at the top of the calf portion (20), which hem or border includes additional material weaved into the fabric but no added stitching as shown in FIG. 1. This seamless construction provides for a blister-free sock that generally will not create blisters or sores on the feet of the wearer.

Figure 2:
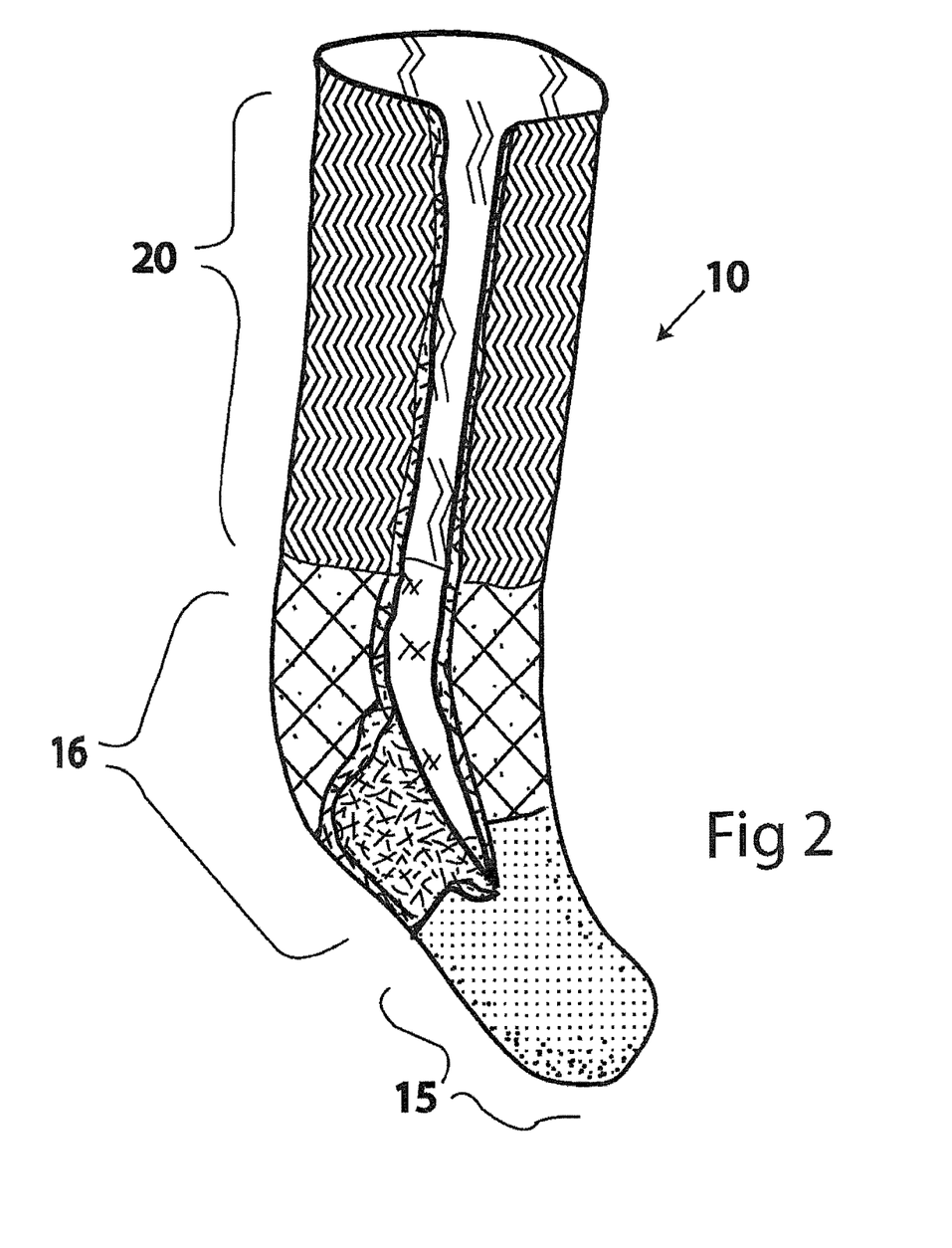
FIG. 2 is a perspective view of the compression sock with simulated compression graduations
Figure 8:
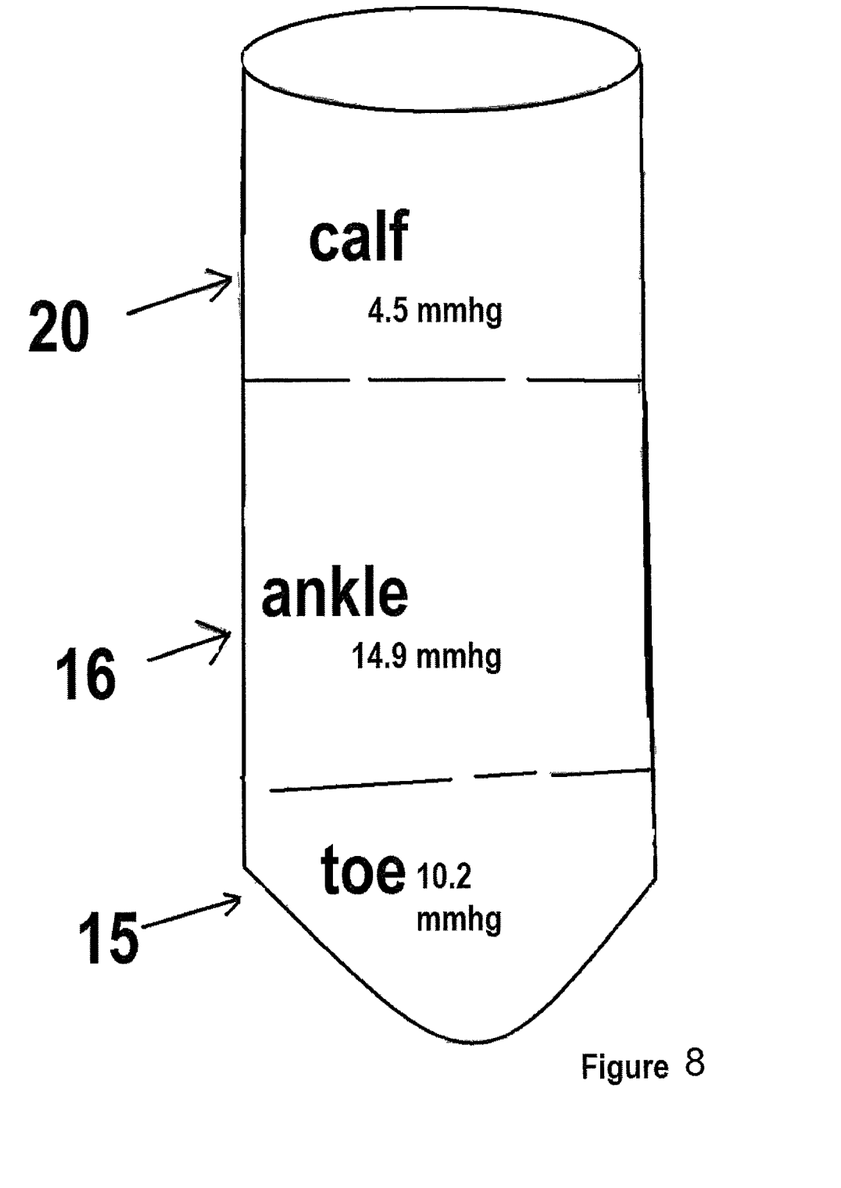
FIG. 8 is a diagram of the graduated compression of the tubular sock.

The entire sock is preferably constructed from a yarn softer composite blend of material. Referring to FIG. 2, the different portions of the sock preferably have varying densities of compression materials. This greater degree of compression provides support similar to tape, a bandage or a sleeve without the drawbacks of adhesive residue, seams or thickened areas that can damage or injure the foot/ankle. The greater degree of compression in the ankle portion is designed to provide support to the ankle joint and its related ligaments. Such support can aid a wearer in decreasing venous pressure and relieve aching legs. This compressive pressure can also be used for relief from minor swelling and varicose veins. As illustrated in FIGS. 2 and 8 the compression structure can have the following (a) toe portion (15) is approximately 10.2 mmgh (b) ankle portion (16) is approximately (14.9) mmgh and (c) calf portion (20) is approximately (4.5) mmgh. As illustrated in the ankle portion (16) has the greatest compression level. The graduated compression provides relief.

The other portions of the sock (10) preferably have their own compressive qualities, but to a lesser degree than the ankle portion. In particular, the calf and the foot portions want to avoid providing too much compression so as not to cut off circulation to tissue in these parts of the foot. The proper amount of compressive pressure in these areas can actually promote proper blood flow during physical activity. The calf and foot portions may have similar compressive qualities. Referring to FIG. 2, these varying compressive qualities are represented by the different densities of stippling in the different portions. Preferably, the portions of the sock (10) other than the ankle portion (16) have a compressive pressure is between 4 grams (16). The same provides relief from tired aching legs, and may help control minor swelling. Most preferably, the ankle portion (16) may be between 30 to 60% tighter than the calf portion (20). In this illustrated embodiment, the sock (10) can be made of floating stitch of 50/34 nylon and 70 denier spandex with 30/34 nylon single covered microfiber.

Figure 6:
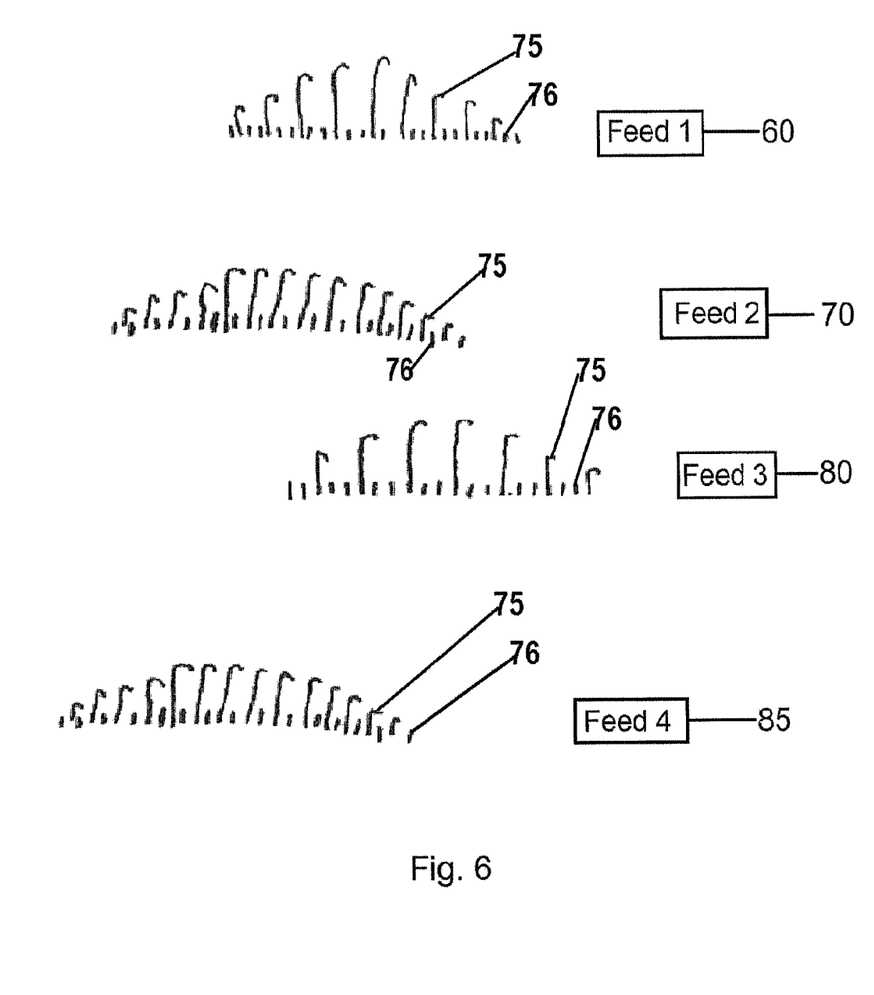
FIG. 6 is a perspective view of the needle positioning in the machinery.
Figure 7:
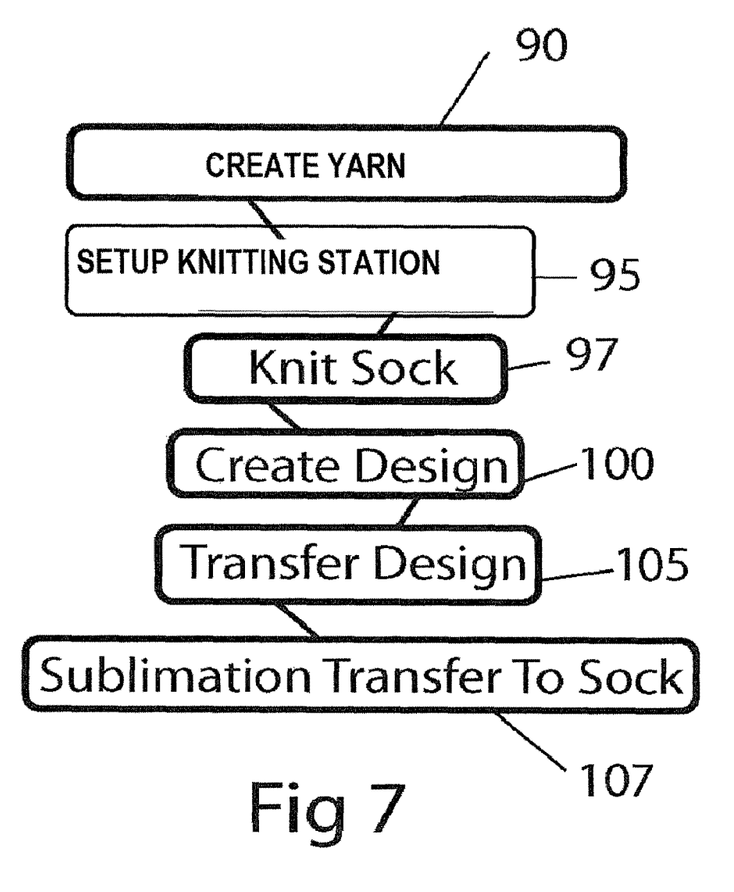
FIG. 7 is a block diagram of the process to create the compression tubular sock.

According to the preferred embodiment, referring to FIG. 7, at step 90 the composite yarn selection is created. Then at step 95 the knitting machine with 400 needles is setup as shown in FIG. 6 to support the alternative positive float selection. The tubular sock (10) in FIG. 1 is created at step 97. After the tubular sock (10) is created utilizing the yarn structure as defined above in steps 90, 95 and 97, the decoration of the compression sock (10) illustrated in FIG. 1 is produced through the process of sublimation. The composite yarn blend allows the tubular sock (10) to better absorb the print while providing a comfortable covering structure over the skin of the leg or the arm. An aesthetically pleasing image is stored on a sublimation transfer medium or sublimation paper at step (100) to create the selected design. The transfer medium is normally a polymer coated transfer paper. The image is transferred from the sublimation transfer medium onto the strip wherein the image is permanently incorporated into the fibers of the material at step (105). The sublimation process is generally done by heat activation which can be at 400 degrees. The heat causes the image to flash into a gaseous state thereby penetrating and dying the image into the material of the compression sock. Through the sublimation process, the image becomes part of the material at step (107).

Although sublimation process is utilized in the preferred embodiment, any equivalent transferal process where the selected design can be incorporated into the material of the tubular sock can be utilized.

What is claimed is:

1. A method for generating a compression tubular sock with a decorative image:
    providing a plurality of yarn feeds wherein each yarn feed is made from a composite blend of fibers selected from the group of nylon, spandex, and microfibers or a combination thereof forming a thin, elastic stretchable and flexible material with a thinner denier that is equivalent to normal hosiery; providing a ladies hosiery knitting machine with a plurality of needle paths set to an alternative stitch selection wherein a smooth finish tubular sock with a relatively thin depth is generated that can be easily placed a user's foot; operationally setting the knitting machine to generate graduated compression; operationally engaging each of the plurality of yarn feeds with a corresponding needle path the; utilizing the knitting machine, generating an integrally formed tubular sock defined by a no heel, closed toe portion, an ankle portion, and an opened calf portion having a graduated variable compression strength, generating the ankle portion with the most level of compression; providing a selected design incorporated into a transfer medium, operationally engaging the transfer medium with an associated transfer device wherein the selected design is permanently transferred from the transfer medium into the fibers of the tubular sock.

2. The method of claim 1 wherein the operationally engaging step further comprises alternating each of the plurality of yarn feeds in association and cooperation with alternating each of the plurality of needle paths positioning wherein a graduated compression tubular sock is created.

3. The method of claim 1 wherein the plurality of needle paths further comprises:
  a first feed, a second feed, a third feed and a fourth feed with each having a plurality of needles; placing the plurality of needles on the first feed in alternating positions;
  operationally placing the plurality of needles on the third feed in alternating positions apposite from the first feed;
  operationally placing the second feed and the fourth feed in opposite alternating positions.

4. The method of claim 3 wherein the plurality of needles of the first feed are set alternating upward and then downward.

5. The method of claim 3 wherein the plurality of needles of the third feed are set alternating downward and then upward.

6. The method of claim 3 wherein the plurality of needles of the second feed are set upward.

7. The method of claim 1 wherein the alternative stitch selection is selected from alternative positive float or flat stitching.

8. The method of claim 1 wherein the means for incorporating further comprises:
  providing a sublimation machine with a storage memory electronically connected therewith;
  selecting a desired design image,
  storing the desired design image in the storage memory; and
  transferring the decorative image from the storage memory into the plurality of fibers of the tubular sock wherein the decorative image become permanently incorporated into the plurality of fibers of the tubular sock.

9. The method of claim 7 wherein the transferring step further comprises transferring the decorative image from the storage memory onto a sublimation material.

10. The method of claim 8 wherein the transferring step further comprises applying heat to transfer the image from the sublimation material into the fibers of the tubular sock.

11. The method of claim 1 wherein each of the plurality of yarn feeds is selected from the group consisting of a spandex of 70 denier with 30/34 filaments of micro fiber covering, a nylon of 50 denier with 34 filaments.

12. The method of claim 1 wherein the composite blend of fibers is the nylon of at least 50/34 filaments.

13. The method of claim 11 wherein the composite blend fibers of a spandex is single covered.

14. The method of claim 1 wherein the composite blend of fibers is a micro fiber selected from the group consisting of nylon, polyester or a combination thereof.

15. The method of claim 1 wherein the toe portion has a compression of at least 10.2 mmgh.

16. The method of claim 1 wherein the ankle portion has a compression of at least 14.9 mmgh.

17. The method of claim 1 wherein the calf portion has a compression of at least 4.5 mmgh.

18. A method for generating a compression tubular arm sock with a decorative image:
  providing a plurality of yarn feeds made from a composite blend of materials that is made of a thin, elastic stretchable and flexible material;
  providing a ladies hosiery knitting machine with a plurality of needle paths set to an alternative positive float selection wherein a smooth finish tubular sock with a relatively thin depth is generated that can be easily placed a user's arm;
  operationally setting the knitting machine to generate graduated compression;
  operationally engaging the plurality of yarn feeds with the plurality of needle paths; utilizing the knitting machine, generating an integrally formed tubular sock defined by an opened lower portion and opened upper portion having a graduated variable compression strength, providing a selected design incorporated into a transfer medium; operationally engaging the transfer medium with an associated transfer device wherein the selected design is permanently transferred from the material into the fibers of the tubular sock.

* * * * *